United States Patent [19]
Kanbe et al.

[11] Patent Number: 5,654,002
[45] Date of Patent: Aug. 5, 1997

[54] PIROXICAM TABLETS AND PRODUCTION AND PROCESS THEREOF

[75] Inventors: Hideyoshi Kanbe, Ichikawa; Youichi Nakajima, Narashino; Akira Iwasa, Yotsukaido, all of Japan

[73] Assignee: SS Pharmaceutical Co., Ltd., Tokyo, Japan

[21] Appl. No.: 466,832

[22] Filed: Jun. 6, 1995

Related U.S. Application Data

[63] Continuation of Ser. No. 270,799, Jul. 5, 1994, abandoned, which is a continuation of Ser. No. 53,358, Apr. 28, 1993, abandoned.

[30] Foreign Application Priority Data

Apr. 28, 1992 [JP] Japan ................... 4-109756

[51] Int. Cl.$^6$ .................................................. A61K 9/20
[52] U.S. Cl. ..................... 424/464; 424/488; 424/499
[58] Field of Search ............................ 424/464, 471, 424/488, 499

[56] References Cited

U.S. PATENT DOCUMENTS

| | | | |
|---|---|---|---|
| 3,591,584 | 7/1971 | Lombardino | 544/49 |
| 4,493,822 | 1/1985 | Tovey | 424/464 |
| 4,808,413 | 2/1989 | Joshi et al. | 424/499 |
| 5,026,560 | 6/1991 | Makino et al. | 424/489 |
| 5,085,869 | 2/1992 | Olthoff et al. | 424/499 |

FOREIGN PATENT DOCUMENTS

| | | |
|---|---|---|
| 0 190 851 | 8/1986 | European Pat. Off. |
| 0 379 579 | 8/1990 | European Pat. Off. |
| 2 585 948 | 2/1987 | France |
| 61 171 | 8/1970 | Luxembourg |
| 2 224 207 | 5/1990 | United Kingdom |

OTHER PUBLICATIONS

Database WPI, Derwent Publications Ltd., AN 92–072430, ZA-A-8 904 558, Dec. 24, 1991.

*Primary Examiner*—Amy Hulina
*Attorney, Agent, or Firm*—Oblon, Spivak, McClelland, Maier & Neustadt, P.C.

[57] ABSTRACT

A process is provided for the production of piroxicam tablets. According to the process, a solution of a water-soluble high-molecular substance is added to a mixture of piroxicam and lactose. The resultant mixture is granulated and then compressed into tablets.

1 Claim, 3 Drawing Sheets

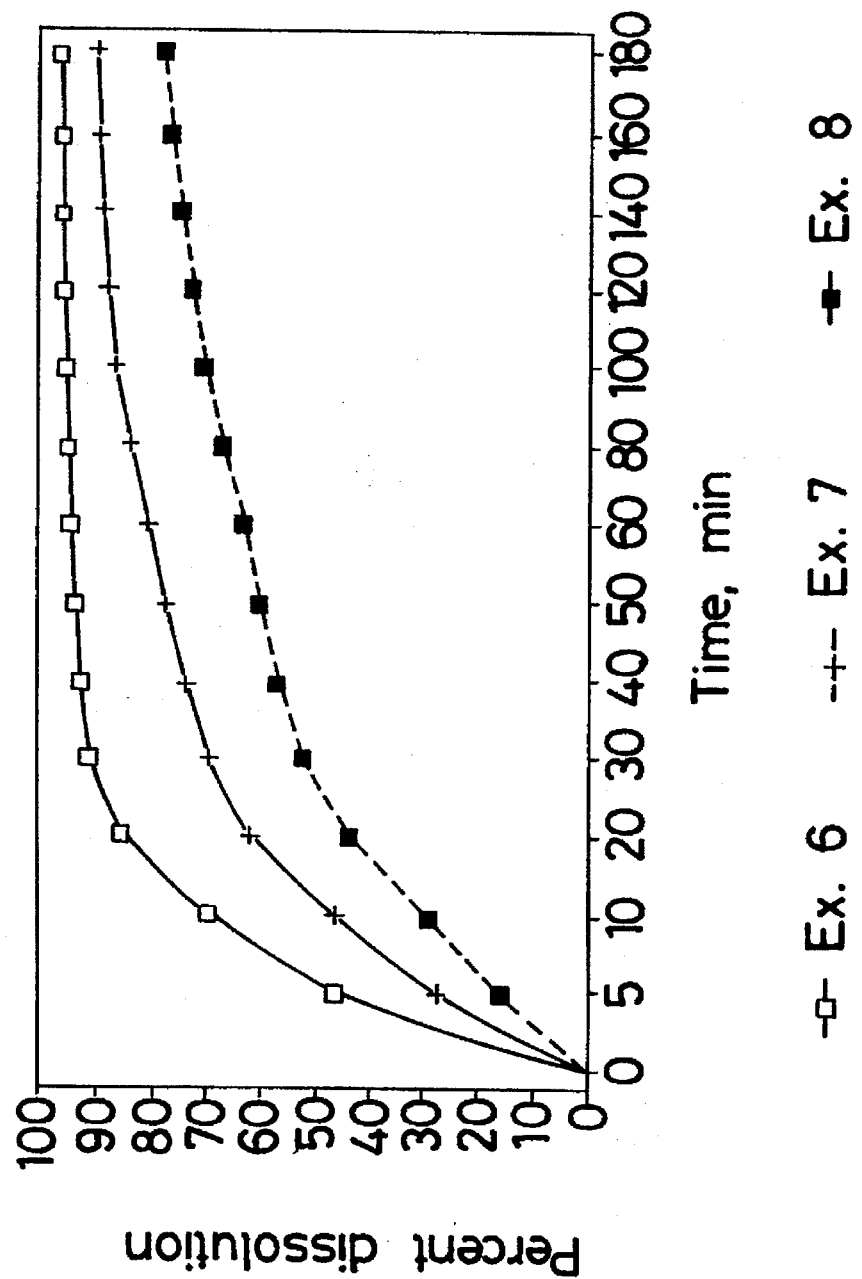

PIROXICAM TABLETS AND PRODUCTION AND PROCESS THEREOF

This application is a continuation of application Ser. No. 08/270,799 filed on Jul. 5, 1994, now abandoned, which is a continuation of Ser. No. 08/053,358 filed on Apr. 28, 1993 now abandoned.

BACKGROUND OF THE INVENTION

1) Field of the Invention

The present invention relates to tablets featuring good dissolution and absorption of piroxicam and a production process thereof.

2) Description of the Related Art

Piroxicam is a non-steroidal anti-inflammatory agent having excellent antiphlogistic, analgesic and antipyretic effects and is now commercially-available as capsules. It remains at an effective blood concentration when administered only once a day and is therefore a long-acting, excellent therapeutic.

Piroxicam, however, is insoluble in water so that no sufficient absorption is feasible when administered as is. Accordingly, piroxicam is commercially sold in the form of capsules filled with fine-particulate piroxicam ground to several microns to 10 microns or so.

Owing to the inclusion of a compression step by a tableting machine, tablets, on the other hand, are compact compared with capsules even at the same drug content so that the former are more palatable. Accordingly, tablets are often more preferred to capsules, resulting in a strong desire for the development of tablets on piroxicam too.

When tablets are formed by direct compression or wet compression by using piroxicam having the same particle size as that filled in capsules, the tablets so obtained are however accompanied by the drawback that they have poor dissolution and insufficient absorption compared with the capsules.

For the improvement of the dissolution of piroxicam, some methods have been proposed to date, including those using piroxicam as a salt with arginine or lysine (European Patent Publication No. 66458), as a salt with ethylene diamine, monoethanol amine or diethanol amine (European Patent Publication No. 66459) and as a composition with natural albumin (Japanese Patent Laid-Open No. 88522/1990).

However, these methods all relate to injections, ointments and/or creams. No method has yet been found to improve the dissolution and absorption of piroxicam when administered in the form of tablets.

SUMMARY OF THE INVENTION

Accordingly, an object of the present invention is to provide piroxicam-containing tablets featuring good dissolution and absorption of piroxicam.

In view of the foregoing circumstances, the present inventors have carried out an extensive investigation with a view toward obtaining piroxicam-containing tablets having good absorption. As a result, it has been found that tablets with good dissolution and absorption can be obtained by adding a solution of a water-soluble high-molecular substance to a mixture of piroxicam and lactose, granulating the resultant mixture and then tableting the thus-obtained granules in a manner known per se in the art, leading to the completion of the invention.

Namely, the present invention provides a process for producing piroxicam tablets, which comprises adding a solution of a water-soluble high-molecular substance to a mixture of piroxicam and lactose, granulating the resultant mixture and then tableting granules so obtained.

Piroxicam tablets obtained employing the production process according to the present invention have, similar to piroxicam capsules, good dissolution and absorption.

BRIEF DESCRIPTION OF THE DRAWINGS

FIG. 3 diagrammatically shows the result of the dissolution test in Test 3.

DETAILED DESCRIPTION OF THE INVENTION AND PREFERRED EMBODIMENTS

Figure 1:
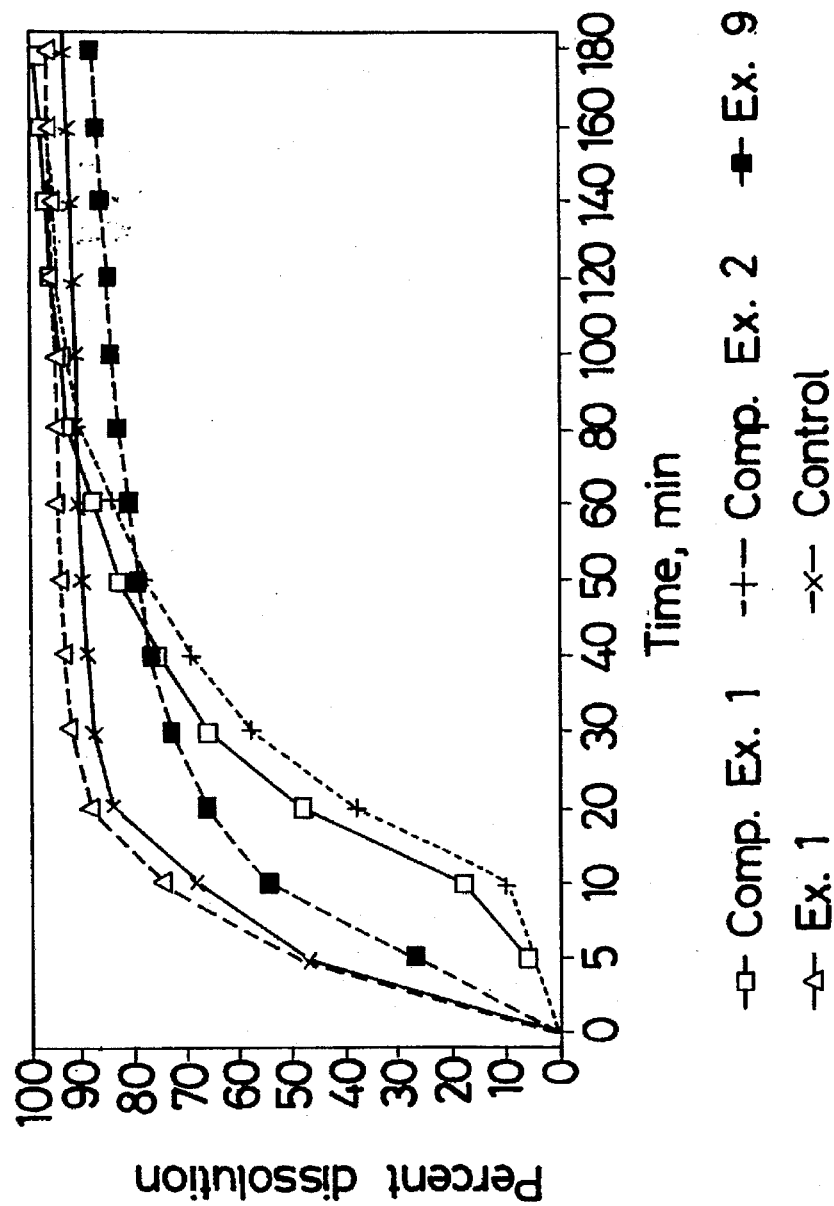
FIG. 1 diagrammatically shows the result of the dissolution test in Test 1.

Any lactose can be employed in the present invention without any particular limitation so long as it can be used for pharmaceuticals. To lactose in the form of large crystals, that in the form of powder having a small particle size is preferred. Preferably, lactose can be used in an amount 2.5–20 times by weight as much as piroxicam, with 3–6 times by weight being particularly preferred.

Incidentally, the advantages of the present invention are considered to be specific to lactose, because saccharides other than lactose, such as sucrose and D-mannitol, cannot bring about the advantages of the present invention.

Examples of the water-soluble high-molecular substance used in the present invention include hydroxypropyl cellulose, polyvinyl pyrrolidone and hydroxypropyl methylcellulose. It is desired to add the water-soluble high-molecular substance in an amount 0.03–0.1 time by weight, particularly 0.03–0.06 time by weight, as much as piroxicam. The water-soluble high-molecular substance is used in a form dissolved in a solvent. Any solvent can be employed for this purpose without any particular limitation insofar as it can dissolve the water-soluble high-molecular substance therein. Examples of such a solvent include organic solvents such as ethanol, methanol and methylene chloride. Among them, ethanol is particularly preferred in view of the fact that the final product is a pharmaceutical.

For the production of tablets according to the present invention, lactose is firstly mixed with piroxicam. It is preferable to employ piroxicam having a particle size of 1–10 μm. The mixing of piroxicam with lactose can be conducted preferably in a stirring-type mixer such as vertical granulator or a twin-cylinder mixer. A solution of a water-soluble high-molecular substance is then added to the resulting mixture, followed by granulation. No particular limitation is imposed on the granulating means. For instance, it is preferable to stir and granulate the mixture in the stirring-type mixer used for the above mixing or to granulate it in a fluidized-bed granulator.

The granules so obtained can be formed into tablets in a manner known per se in the art. An excipient commonly used for pharmaceuticals, such as microcrystalline cellulose (for example, "AVICEL PH301", trade name) or lactose and a lubricant such as talc are added to the granules, and the resultant mixture is then subjected to direct compression, whereby piroxicam tablets of the present invention can be obtained. In this case, a disintegrator such as starch can also be added. Alternatively, tablets can also be produced by wet compression.

The present invention will next be described in detail by the following examples. It should however be borne in mind that this invention is by no means limited to or by the examples.

Piroxicam tablets and the like were produced as will be described in Examples 1–9, Comparative Examples 1–2 and Control.

EXAMPLE 1

| Composition: | (per tablet) |
| --- | --- |
| Piroxicam | 20 mg |
| Lactose | 100 |
| Hydroxypropylcellulose | 0.9 |
| Sub-total | 120.9 mg |
| AVICEL PH301 | 16 |
| Crystalline lactose | 20.7 |
| Talc | 0.8 |
| Magnesium stearate | 1.6 |
| Total | 160 mg |

Procedures:

Out of the above ingredients, 400 g of piroxicam and 2000 g of lactose were weighed. They were mixed in a mixer (vertical granulator, "FM-VG-25", trade name; manufactured by Powreck Corp). The resultant mixture was stirred and granulated in the presence of 360 g of a 5% ethanol solution of hydroxypropylcellulose. The resultant granules were dried at 50° C., followed by the addition of "AVICEL PH301", crystalline lactose (100M), talc and magnesium stearate. The mixture so formed was compressed using a rotary tableting machine ("RT-S15-T35", trade name; manufactured by Kikusui Seisakusho, Ltd.), whereby flat tablets having a diameter of 7 mm and weighing 160 mg each were obtained.

EXAMPLE 2

| Composition: | (per tablet) |
| --- | --- |
| Piroxicam | 20 mg |
| Lactose | 80 |
| Hydroxypropylcellulose | 0.7 |
| Sub-total | 100.7 mg |
| AVICEL PH301 | 1.2 |
| Crystalline lactose | 1.6 |
| Talc | 0.5 |
| Magnesium stearate | 1.0 |
| Total | 105 mg |

Procedures:

Out of the above ingredients, 400 g of piroxicam and 1600 g of lactose were weighed. They were mixed in the mixer (vertical granulator, "FM-VG-25", trade name; manufactured by Powreck Corp). The resultant mixture was stirred and granulated in the presence of 280 g of a 5% ethanol solution of hydroxypropylcellulose. In a similar manner to Example 1, flat tablets having a diameter of 7 mm and weighing 105 mg each were obtained.

EXAMPLE 3

| Composition: | (per tablet) |
| --- | --- |
| Piroxicam | 20 mg |
| Lactose | 60 |
| Hydroxypropylcellulose | 0.7 |
| Sub-total | 80.7 mg |
| AVICEL PH301 | 10.0 |
| Crystalline lactose | 12.8 |
| Talc | 0.5 |
| Magnesium stearate | 1.0 |
| Total | 105 mg |

Procedures:

Out of the above ingredients, 800 g of piroxicam and 2400 g of lactose were weighed. They were mixed in the mixer (vertical granulator, "FM-VG-25", trade name; manufactured by Powreck Corp.). The resultant mixture was stirred and granulated in the presence of 560 g of a 5% ethanol solution of hydroxypropylcellulose. In a similar manner to Example 1, flat tablets having a diameter of 7 mm and weighing 105 mg each were obtained.

EXAMPLE 4

| Composition: | (per tablet) |
| --- | --- |
| Piroxicam | 20 mg |
| Lactose | 40 |
| Hydroxypropylcellulose | 0.5 |
| Sub-total | 60.5 mg |
| AVICEL PH301 | 18 |
| Crystalline lactose | 25 |
| Talc | 0.5 |
| Magnesium stearate | 1.0 |
| Total | 105 mg |

Procedures:

Out of the above ingredients, 800 g of piroxicam and 1600 g of lactose were weighed. They were mixed in the mixer (vertical granulator, "FM-VG-25", trade name; manufactured by Powreck Corp.). The resultant mixture was stirred and granulated in the presence of 400 g of a 5% ethanol solution of hydroxypropylcellulose. In a similar manner to Example 1, flat tablets having a diameter of 7 mm and weighing 105 mg each were obtained.

EXAMPLE 5

| Composition: | (per tablet) |
| --- | --- |
| Piroxicam | 20 mg |
| Lactose | 20 |
| Hydroxypropylcellulose | 0.4 |
| Sub-total | 40.4 mg |
| AVICEL PH301 | 26.1 |
| Crystalline lactose | 37.0 |
| Talc | 0.5 |
| Magnesium stearate | 1.0 |
| Total | 105 mg |

Procedures:

Out of the above ingredients, 800 g of piroxicam and 800 g of lactose were weighed. They were mixed in the mixer (vertical granulator, "FM-VG-25", trade name; manufactured by Powreck Corp.). The resultant mixture was stirred and granulated in the presence of 320 g of a 5% ethanol solution of hydroxypropylcellulose. In a similar manner to Example 1, flat tablets having a diameter of 7 mm and weighing 105 mg each were obtained.

EXAMPLE 6

| Composition: | (per tablet) |
|---|---|
| Piroxicam | 20 mg |
| Lactose | 60 |
| Hydroxypropylcellulose | 0.7 |
| Sub-total | 80.7 mg |
| AVICEL PH301 | 2.0 |
| Crystalline lactose | 1.1 |
| Talc | 0.4 |
| Magnesium stearate | 0.8 |
| Total | 85 mg |

Procedures:

Out of the above ingredients, 800 g of piroxicam and 2,400 g of lactose were weighed. They were mixed in the mixer (vertical granulator, "FM-VG-25", trade name; manufactured by Powreck Corp). The resultant mixture was stirred and granulated in the presence of 560 g of a 5% ethanol solution of hydroxypropylcellulose. In a similar manner to Example 1, flat tablets having a diameter of 6 mm and weighing 85 mg each were obtained.

EXAMPLE 7

| Composition: | (per tablet) |
|---|---|
| Piroxicam | 20 mg |
| Lactose | 40 |
| Hydroxypropylcellulose | 0.5 |
| Sub-total | 60.5 mg |
| AVICEL PH301 | 10.0 |
| Crystalline lactose | 13.3 |
| Talc | 0.4 |
| Magnesium stearate | 0.8 |
| Total | 85 mg |

Procedures:

Out of the above ingredients, 800 g of piroxicam and 1,600 g of lactose were weighed. They were mixed in the mixer (vertical granulator, "FM-VG-25", trade name; manufactured by Powreck Corp.). The resultant mixture was stirred and granulated in the presence of 400 g of a 5% ethanol solution of hydroxypropylcellulose. In a similar manner to Example 1, flat tablets having a diameter of 6 mm and weighing 85 mg each were obtained.

EXAMPLE 8

| Composition: | (per tablet) |
|---|---|
| Piroxicam | 20 mg |
| Lactose | 20 |
| Hydroxypropylcellulose | 0.4 |
| Sub-total | 40.4 mg |
| AVICEL PH301 | 18.0 |
| Crystalline lactose | 25.4 |
| Talc | 0.4 |

-continued

| Composition: | (per tablet) |
|---|---|
| Magnesium stearate | 0.8 |
| Total | 85 mg |

Procedures:

Out of the above ingredients, 800 g of piroxicam and 800 g of lactose were weighed. They were mixed in the mixer (vertical granulator, "FM-VG-25", trade name; manufactured by Powreck Corp.). The resultant mixture was stirred and granulated in the presence of 320 g of a 5% ethanol solution of hydroxypropylcellulose. In a similar manner to Example 1, flat tablets having a diameter of 6 mm and weighing 85 mg each were obtained.

EXAMPLE 9

| Composition: | (per tablet) |
|---|---|
| Piroxicam | 20 mg |
| Lactose | 76 |
| AVICEL PH301 | 60 |
| Hydroxypropylcellulose | 1.8 |
| Talc | 0.6 |
| Magnesium stearate | 1.6 |
| Total | 160 mg |

Procedures:

Out of the above ingredients, 400 g of piroxicam, 1520 g of lactose and 1200 g of AVICEL PH301 were weighed. They were mixed in the mixer (vertical granulator, "FM-VG-25", trade name; manufactured by Powreck Corp.). The resultant mixture was stirred and granulated in the presence of 720 g of a 5% ethanol solution of hydroxypropylcellulose. The resultant granules were dried at 50° C., followed by the addition of talc and magnesium stearate. The mixture so formed was compressed using the rotary tableting machine ("RT-S15-T35", trade name; manufactured by Kikusui Seisakusho, Ltd.), whereby flat tablets having a diameter of 7 mm and weighing 160 mg each were obtained. The tablets so obtained will be designated as the tablets of Example 9 produced by wet compression.

Comparative Example 1

| Composition: | (per tablet) |
|---|---|
| Piroxicam | 20 mg |
| Lactose | 80 |
| AVICEL PH301 | 58.6 |
| Talc | 0.6 |
| Magnesium stearate | 0.8 |
| Total | 160 mg |

Procedures:

The above ingredients were weighed to give a total amount of 3200 g. They were mixed for 20 minutes in a twin-cylinder mixer ("V-10" type; manufactured by Tokuju Seisakusho Co., Ltd.). The resulting mixture was compressed by the rotary tableting machine ("RT-S15-T35", trade name; manufactured by Kikusui Seisakusho, Ltd.), whereby flat tablets having a diameter of 7 mm and weighing 160 mg each were obtained. The tablets so obtained will be designated as the tablets of Comparative Example 1 produced by direct compression.

Comparative Example 2

| Composition: | (per tablet) |
|---|---|
| Piroxicam | 20 mg |
| Lactose | 120 |
| AVICEL PH301 | 18.6 |
| Talc | 0.6 |
| Magnesium stearate | 0.8 |
| Total | 160 mg |

Procedures:

The above ingredients were weighed to give a total amount of 3200 g. They were mixed for 20 minutes in the twin-cylinder mixer ("V-10" type, manufactured by Tokuju Seisakusho Co., Ltd.). The resulting mixture was compressed by the rotary tableting machine ("RT-S15-T35", trade name; manufactured by Kikusui Seisakusho, Ltd.), whereby flat tablets having a diameter of 7 mm and weighing 160 mg each were obtained. The tablets so obtained will be designated as the tablets of Comparative Example 2 produced by direct compression.

Control (capsules)

| Composition: | (per capsule) |
|---|---|
| Piroxicam | 20 mg |
| Lactose | 320.2 |
| Corn starch | 18 |
| Talc | 1.8 |
| Total | 360 mg |

Procedures:

The above ingredients were weighed to give a total amount of 3600 g. They were mixed for 20 minutes in the twin-cylinder mixer ("V-10" type, manufactured by Tokuju Seisakusho Co., Ltd.). The resulting mixture was filled in No. 2 capsules by a Park-Davis capsule filling machine, whereby capsules were obtained.

Test 1

A dissolution test of the piroxicam tablets and capsules, which had been obtained in Examples 1 and 9, Comparative Examples 1 and 2 and Control, was conducted by the paddle process (rotational speed: 100 rpm, test solution: water).

The results are shown in Table 1 and FIG. 1.

TABLE 1

Results of Dissolution Test 1

| Time (minutes) | Comp. Ex. 1 Direct compression | Comp. Ex. 2 Direct compression | Example 9 Wet Compression | Example 1 Process according to this invention | percent dissolution Control Capsule filled with mixed powder |
|---|---|---|---|---|---|
| 0 | 0 | 0 | 0 | 0 | 0 |
| 5 | 6.0 | 5.0 | 27.2 | 50.2 | 48.2 |
| 10 | 18.1 | 10.2 | 54.8 | 72.9 | 68.2 |
| 20 | 48.2 | 38.5 | 66.3 | 87.0 | 83.9 |
| 30 | 66.0 | 57.8 | 72.9 | 90.9 | 87.8 |
| 40 | 75.5 | 69.5 | 76.8 | 92.2 | 89.0 |
| 50 | 82.6 | 77.7 | 78.7 | 93.2 | 89.8 |
| 60 | 87.8 | 83.7 | 80.6 | 94.4 | 90.3 |
| 80 | 93.2 | 90.2 | 83.0 | 94.8 | 91.0 |
| 100 | 95.0 | 93.1 | 84.0 | 95.6 | 91.4 |
| 120 | 96.4 | 94.5 | 85.1 | 96.8 | 92.0 |
| 140 | 97.5 | 95.6 | 86.2 | 96.9 | 92.3 |
| 160 | 98.3 | 96.6 | 87.2 | 97.0 | 92.8 |
| 180 | 99.3 | 97.8 | 88.1 | 97.2 | 93.6 |

From the results of the above test, it is understood that the tablets of Comparative Examples 1 and 2, are inferior in dissolution because they contain no water-soluble high-molecular substances. It is also understood that, compared with them, the tablets of Examples 1 and 9 and the capsules have excellent dissolution.

Test 2

Figure 2:
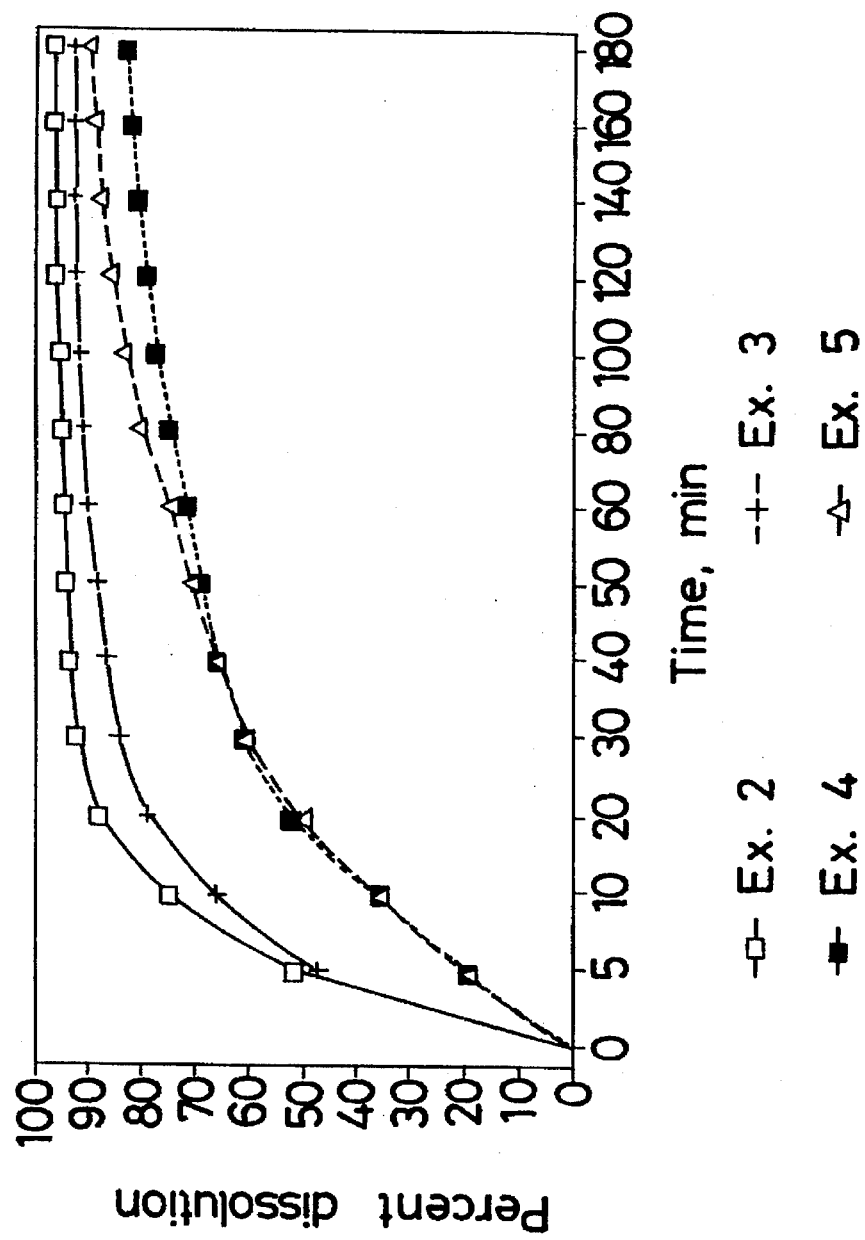
FIG. 2 diagrammatically shows the result of the dissolution test in Test 2.

In a similar manner to Test 1, a dissolution test was conducted on the tablets obtained in Examples 2–5. The results are shown in Table 2 and FIG. 2.

TABLE 2

Results of Dissolution Test 2

| Time (minutes) | Example 2 | Example 3 | Percent dissolution Example 4 | Example 5 |
|---|---|---|---|---|
| 0 | 0 | 0 | 0 | 0 |
| 5 | 51.2 | 48.0 | 18.5 | 20.2 |
| 10 | 74.9 | 66.4 | 34.7 | 36.7 |
| 20 | 88.0 | 79.3 | 52.4 | 49.9 |
| 30 | 91.9 | 84.4 | 60.7 | 60.2 |
| 40 | 93.2 | 86.6 | 65.6 | 66.2 |
| 50 | 94.2 | 88.4 | 69.0 | 71.3 |
| 60 | 94.6 | 90.6 | 71.6 | 74.9 |
| 80 | 94.9 | 91.3 | 74.7 | 80.0 |
| 100 | 95.5 | 92.0 | 77.2 | 83.4 |
| 120 | 96.1 | 92.6 | 78.9 | 85.8 |
| 140 | 95.9 | 92.8 | 80.5 | 87.5 |
| 160 | 96.2 | 92.6 | 81.7 | 88.8 |
| 180 | 96.4 | 92.6 | 82.6 | 90.2 |

As can been seen from the above results, the tablets of Examples 2 and 3 which contain piroxicam and lactose at weight ratios of 1:4 and 1:3, respectively, show a dissolution velocity higher than the tablets of Examples 4 and 5 which contain piroxicam and lactose at weight ratios of 1:2 and 1:1, respectively.

Test 3

The tablets obtained in Examples 6–8 were subjected to a dissolution test in a similar manner to Test 1. The results are shown in Table 3 and FIG. 3.

TABLE 3

Results of Dissolution Test 3

| Time (minutes) | Example 6 | Example 7 | Percent dissolution Example 8 |
|---|---|---|---|
| 0 | 0 | 0 | 0 |
| 5 | 46.2 | 27.6 | 15.9 |
| 10 | 69.5 | 46.4 | 28.7 |
| 20 | 85.1 | 62.4 | 43.2 |
| 30 | 90.8 | 69.4 | 51.8 |
| 40 | 92.4 | 73.4 | 56.5 |
| 50 | 93.4 | 76.9 | 59.8 |
| 60 | 93.8 | 80.0 | 62.6 |
| 80 | 94.5 | 83.4 | 66.4 |
| 100 | 94.8 | 85.9 | 69.7 |
| 120 | 94.9 | 87.0 | 72.0 |
| 140 | 95.4 | 88.0 | 73.8 |
| 160 | 95.6 | 88.8 | 75.6 |
| 180 | 96.0 | 89.2 | 76.8 |

From the above results, it is understood that the tablets of Example 6 containing piroxicam and lactose at a weight ratio of 1:3 have a dissolution velocity higher than the tablets of Examples 7 and 8 containing piroxicam and lactose at weight ratios of 1:2 and 1:1, respectively.

We claim:

1. A process for producing piroxicam tablets, which comprises:

adding a solution of a water-soluble, high-molecular weight substance selected from the group consisting of hydroxypropylcellulose and hydroxypropylmethylcellulose in an amount of 0.03–0.1 times by weight the amount of piroxicam to a mixture of piroxicam and lactose in an amount of 2.5–20 times by weight the amount of piroxicam;

granulating the resultant mixture; and then tableting the granules so obtained.

* * * * *